(12) United States Patent
Aguirre (10) Patent No.: US 8,728,105 B2
(45) Date of Patent: May 20, 2014

(54) ELONGATE MAGNET FOR A MAGNETIC ANASTOMOSIS DEVICE

(75) Inventor: Andres F. Aguirre, Chicago, IL (US)

(73) Assignee: Cook Medical Technologies LLC, Bloomington, IN (US)

(*) Notice: Subject to any disclaimer, the term of this patent is extended or adjusted under 35 U.S.C. 154(b) by 749 days.

(21) Appl. No.: 12/971,906

(22) Filed: Dec. 17, 2010

(65) Prior Publication Data
US 2011/0160752 A1 Jun. 30, 2011

Related U.S. Application Data

(60) Provisional application No. 61/291,202, filed on Dec. 30, 2009.

(51) Int. Cl.
*A61B 17/08* (2006.01)
(52) U.S. Cl.
USPC .............................. 606/153; 606/8
(58) Field of Classification Search
None
See application file for complete search history.

(56) References Cited

U.S. PATENT DOCUMENTS

| | | | |
|---|---|---|---|
| 4,899,744 A * | 2/1990 | Fujitsuka et al. ............ 606/153 |
| 5,690,656 A | 11/1997 | Cope et al. |
| 6,273,917 B1 | 8/2001 | Inoue |
| 6,802,847 B1 | 10/2004 | Carson et al. |
| 6,932,827 B2 | 8/2005 | Cole |
| 2004/0107004 A1 | 6/2004 | Levine et al. |
| 2005/0070821 A1 | 3/2005 | Deal et al. |
| 2005/0080439 A1 | 4/2005 | Carson et al. |
| 2005/0228412 A1 | 10/2005 | Surti |
| 2008/0114384 A1 | 5/2008 | Chang et al. |
| 2009/0125042 A1 | 5/2009 | Mouw |
| 2012/0035628 A1 | 2/2012 | Aguirre et al. |

FOREIGN PATENT DOCUMENTS

| WO | WO 2008/061024 A2 | 5/2008 |
| WO | WO 2010/115116 | 10/2010 |

OTHER PUBLICATIONS

U.S. Office Action dated Jul. 11, 2012 for U.S. Appl. No. 12/753,583.
International Search Report/Written Opinion for PCT/US2010/061083 dated Apr. 21, 2011.
IPRP for PCT/US2010/061083 dated Jul. 4, 2012.
International Search Report/Written Opinion for PCT/US2010/029801 Jun. 16, 2010.
IPRP for PCT/US2010/029801 dated Apr. 3, 2009.

* cited by examiner

*Primary Examiner* — Corrine M McDermott
*Assistant Examiner* — Son Dang
(74) *Attorney, Agent, or Firm* — Brinks Gilson & Lione

(57) ABSTRACT

A magnetic anastomosis device is provided for forming an anastomosis between two bodily walls. The device includes a first magnet assembly and a second magnet assembly configured to be magnetically coupled to compress the two bodily walls therebetween to form the anastomosis. The first magnet assembly includes a first magnet and a second magnet disposed within a first jacket and the second magnet assembly includes a third magnet and a fourth magnet disposed within a second jacket.

18 Claims, 10 Drawing Sheets

ELONGATE MAGNET FOR A MAGNETIC ANASTOMOSIS DEVICE

CROSS-REFERENCE TO RELATED APPLICATIONS

This application claims the benefit of U.S. Provisional Application Ser. No. 61/291,202 filed on Dec. 30, 2009, entitled "ELONGATE MAGNET FOR A MAGIC ANASTOMOSIS DEVICE" the entire contents of which are incorporated herein by reference.

FIELD OF THE INVENTION

The present invention relates generally to magnetic anastomosis devices for forming an anastomosis between two viscera.

BACKGROUND OF THE INVENTION

Magnetic anastomosis devices (MADS) are currently used to create a channel between two viscera for the purpose of redirecting bodily fluids. For example, intestinal contents or bile may be redirected in patients who have developed an obstruction of the bowel or bile duct due to such conditions as tumor, ulcer, inflammatory strictures or trauma. A magnetic anastomosis device is disclosed in U.S. Pat. No. 5,690,656, the disclosure of which is incorporated herein by reference in its entirety. Generally, the MAD includes first and second magnet assemblies comprising magnetic cores that are surrounded by thin metal rims. Due to the magnetic attraction between the two magnetic cores, the walls of two adjacent viscera may be sandwiched and compressed between the magnet assemblies, resulting in ischemic necrosis of the walls to produce an anastomosis between the two viscera. The viscera treated by MADs include the gall bladder, the common bile duct, the stomach, the duodenum, the jejunum of the small intestine, as well as the large intestine and left and right hepatic ducts.

Typically, immediately after formation of the anastomosis, a stent is delivered in the anastomosis to prevent the anastomosis from closing. Thus, forming an anastomosis with current MAD designs, such as the MAD device disclosed in U.S. Pat. No. 5,690,656, generally involves two interventional procedures, the first being placement of the magnet assemblies to create the anastomosis and the second being placement of a stent within the newly formed anastomosis to prevent it from closing.

BRIEF SUMMARY OF THE INVENTION

The present invention provides a magnetic anastomosis device that is minimally invasive, easily and quickly delivered, and is accurately positioned to improve the delivery procedure. According to one embodiment constructed in accordance with the teachings of the present invention, a magnetic anastomosis device used for forming an anastomosis between two bodily walls includes a first magnet assembly and a second magnet assembly configured to be magnetically coupled to compress the two bodily walls therebetween to form the anastomosis. The first magnet assembly includes a first magnet and a second magnet disposed within a first jacket and the second magnet assembly includes a third magnet and a fourth magnet disposed within a second jacket.

According to another embodiment constructed in accordance with the teachings of the present invention, a magnetic anastomosis device used for forming an anastomosis between two bodily walls includes a first magnet, a second magnet, a third magnet, and a fourth magnet. A first jacket encases the first and second magnets and a second jacket encases the third and fourth magnets. The first and second jackets each have an elongate shape defining a first and a second longitudinal axis, respectively. The first and second magnets are oriented on the first longitudinal axis of the first jacket and the third and fourth magnets are oriented on the second longitudinal axis of the second jacket. The first and second jackets are configured to be magnetically coupled to compress the two bodily walls therebetween to form the anastomosis.

BRIEF DESCRIPTION OF THE DRAWINGS

The accompanying drawings incorporated in and forming a part of the specification illustrate several aspects of the present invention, and together with the description serve to explain the principles of the invention. In the drawings:

FIG. 8b is a side view of the magnetic anastomosis device of FIG. 8a;

FIG. 9b is an overhead view of the delivery system of FIG. 9a;

DETAILED DESCRIPTION OF THE INVENTION

Detailed embodiments of the present invention are disclosed herein. It is understood however, that the disclosed embodiments are merely exemplary of the invention and may be embodied in various and alternative forms. The figures are not necessarily to scale; some figures may be configured to show the details of a particular component. Therefore, specific structural and functional details disclosed herein are not to be interpreted as limiting but merely as a representative basis with the claims and for teaching one skilled in the art to practice the present invention.

Figure 1:
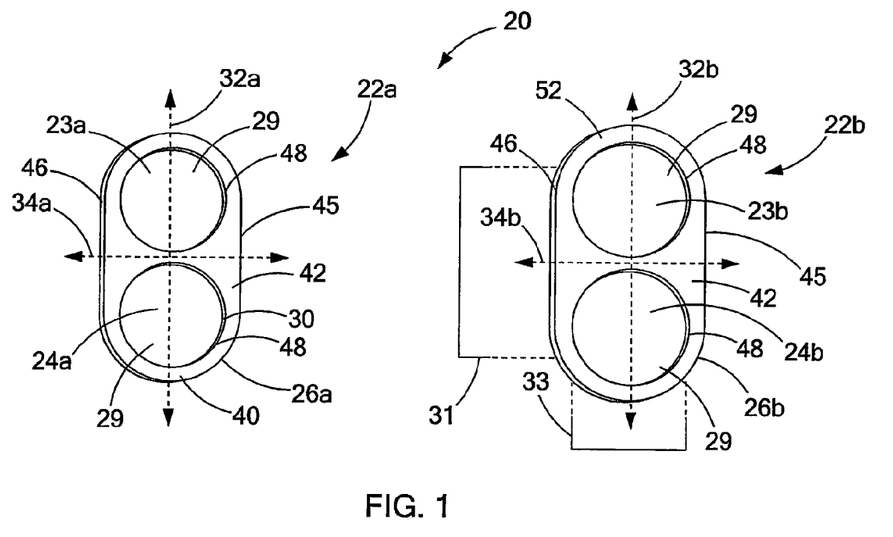
FIG. 1 is a perspective view of two magnet assemblies of a magnetic anastomosis device constructed in accordance with the teachings of the present invention.

Turning now to the figures, FIG. 1 depicts a magnetic anastomosis device 20 that is used to form an anastomosis between two viscera, specifically bodily walls of two adjacent viscera. In one example, an intestinal bypass anastomosis may be used to treat obesity. Generally, the magnetic anastomosis device 20 includes first and second magnet assemblies 22a, 22b configured to be magnetically coupled to compress the bodily walls therebetween to form the anastomosis. In FIG. 1, each of the magnet assemblies 22a, 22b includes two magnets 23a, 24a and 23b, 24b disposed within a respective elongate jacket 26a, 26b. Each of the magnets 23a, 24a, 23b, 24b includes a magnetic core 29 encased within the respective elongate jacket 26a, 26b. It is also within the scope of the present invention for each magnet 23a, 24a, 23b, 24b to include an individual metal or plastic jacket surrounding the magnetic core 29, both of which are encased within the respective elongate jacket 26a, 26b.

The term "elongate" as used herein to describe the shape of the jackets 26a, 26b, or magnet assemblies 22a, 22b, is intended to include an elliptical shape including an ellipse having a major axis and a minor axis; an oval or ovoid shape; an egg shape; a kidney shape; a figure eight shape; or any oblong shape having a continuous peripheral surface. For example, "elongate" may include a rectangle with rounded corners. In another example, the ends of the jackets 26a, 26b may have a tapered rounded nose shape similar to the distal ends of typical dilator catheters known in the art. It is believed that such shapes provide greater comfort and ease during swallowing and/or positioning of the magnet assemblies 22a, 22b within the body of the patient.

Figure 2:
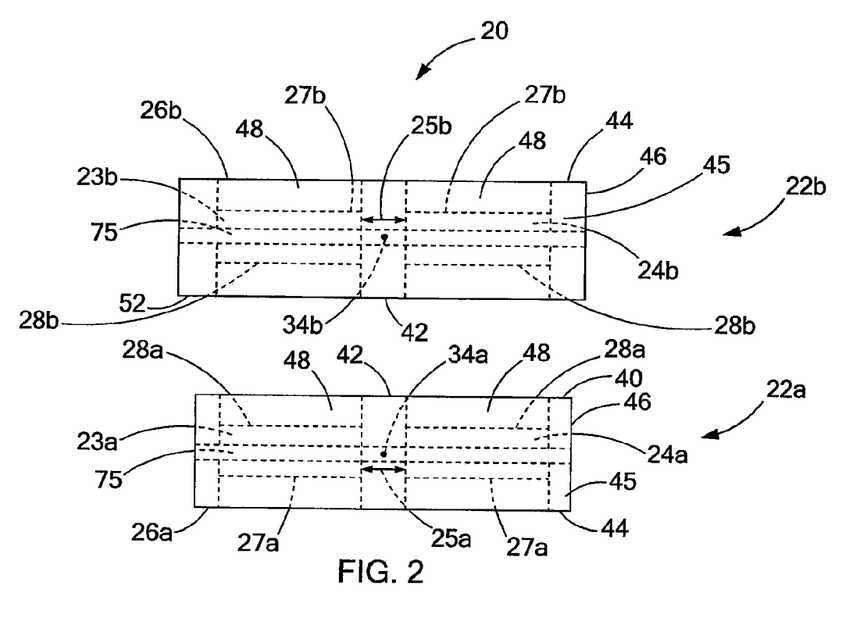
FIG. 2 is a side view of the two magnet assemblies of the magnetic anastomosis device of FIG. 1.
Figure 6:
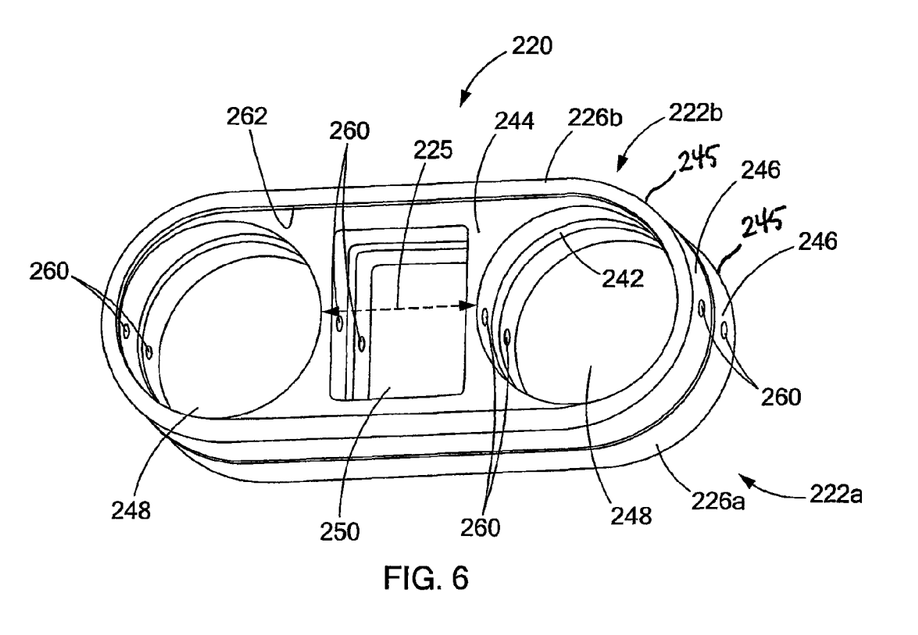
FIG. 6 is a perspective view of a magnetic anastomosis device constructed in accordance with further teachings of the present invention.

As illustrated in FIG. 1, each of the elongate jackets 26a, 26b defines a longitudinal axis 32a, 32b and a lateral axis 34a, 34b. In this embodiment, the magnets 23a, 24a are oriented on the longitudinal axis 32a of the jacket 26a of the first magnet assembly 22a. Similarly, the magnets 23b, 24b are oriented on the longitudinal axis 32b of the jacket 26b of the second magnet assembly 22b. In other words, the magnets 23a, 24a and 23b, 24b, are disposed along the respective longitudinal axis 32a, 32b in a side-by-side arrangement (i.e., as opposed to on top of one another or overlapping). As shown in FIG. 2, the magnets 23a, 24a and 23b, 24b are spaced apart from one another on different sides of the respective lateral axis 34a, 34b, defining a space or gap 25a, 25b between the magnets 23a, 24a and 23b, 24b. The gap 25a, 25b between the magnets 23a, 24a and 23b, 24b may be a small gap, i.e., about 0.5 mm to about 3 mm, or a larger gap as shown in FIG. 6 and described in more detail below. Alternatively, the magnets 23a, 24a and 23b, 24b may be immediately adjacent within their respective jacket 26a, 26b such that there is no space in between the magnets 23a, 24a and 23b, 24b.

Figure 3:
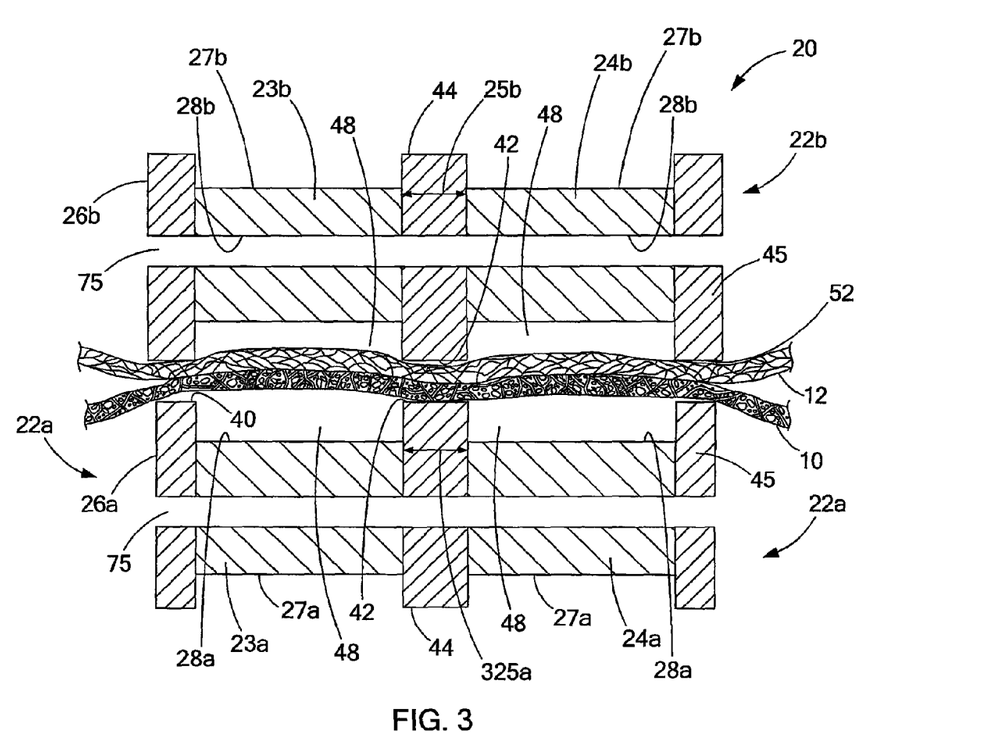
FIG. 3 is a cross-sectional view of the two magnet assemblies of the magnetic anastomosis device of FIG. 1, shown forming an anastomosis.

Referring to FIGS. 2 and 3, each jacket 26a, 26b includes a body portion 45 having first and second opposing planar surfaces 42 and 44 and a peripheral surface 46 extending therebetween. Each body portion 45 includes two cavities 48 formed therethrough by any suitable means in the art. Each cavity 48 is formed through the body portion 45 through the opposing planar surfaces 42 and 44 and is dimensioned to receive one of the magnets 23a, 24a, 23b, 24b such that when the magnets 23a, 24a, 23b, 24b are disposed within their respective jacket 26a, 26b the magnets 23a, 24a, 23b, 24b are recessed from the planar surfaces 42 and 44. The magnets 23a, 24a, 23b, 24b are held within the cavities 48 by any suitable means in the art, for example, via a press-fit engagement or an adhesive.

Preferably, each of the magnet assemblies 22a, 22b includes a lumen 75 formed therethrough to accommodate a suture or a wire guide for delivery purposes, as discussed in further detail below. FIGS. 2 and 3 show the lumen 75 extending through each of the magnet assemblies 22a, 22b, i.e., through the jackets 26a, 26b and each of the magnets 23a, 24a, 23b, 24b. It is noted that, although the lumen 75 extending through of the magnets 23a, 24a, 23b, 24b makes it appear as though there are four separate magnets within each of the magnet assemblies 22a, 22b, only two magnets 23a, 24a are shown within the magnet assembly 22a and only two magnets 23b, 24b are shown within the magnet assembly 22b.

As shown in FIGS. 2 and 3, the magnets 23a, 24a have opposing faces 27a and 28a and the magnets 23b, 24b have opposing faces 27b and 28b. The faces 28a of the magnets 23a, 24a disposed within the jacket 26a of the first magnet assembly 22a have a magnetic attraction to the faces 28b of the magnets 23b, 24b disposed within the jacket 26b of the second magnet assembly 22b. Preferably, one of the faces 28a of the magnets 23a, 24a is north pole and the other is south pole. Similarly, one of the faces 28b of the magnets 23b, 24b is north pole and the other is south pole, the north pole face 28a configured to mate with the south pole face 28b and the south pole face 28a configured to mate with the north pole face 28b. Alternatively, both faces 28a of the magnets 23a, 24a may be north pole and both faces 28b of the magnets 23b, 24b may be south pole, or vice versa, in which case either of the two magnets 23a, 24a can mate with either of the two magnets 23b, 24b. The magnetic attraction between the magnets 23a, 24a and the magnets 23b, 24b causes the magnet assemblies 22a, 22b to move toward one another, thereby capturing a portion of the walls 10, 12 between them. The dual magnets aid in alignment and centering of the magnet assemblies 22a, 22b with respect to one another.

FIG. 3 illustrates the first and second magnet assemblies 22a, 22b coming together to compress the two bodily walls 10, 12 therebetween to form an anastomosis between two hollow organs. Due to the magnetic attraction between the two magnet assemblies 22a, 22b, via the magnets 23a, 24a and 23b, 24b, the bodily walls 10, 12 of two adjacent hollow organs may be sandwiched and compressed between the magnet assemblies 22a, 22b, resulting in ischemic necrosis of the bodily walls 10, 12 to produce the anastomosis. As the magnet assemblies 22a and 22b are drawn toward one another, the peripheral edge 40 of the magnet assembly 22a contacts the wall 10 of the viscera and the peripheral edge 52 of the magnet assembly 22b contacts the wall 12 of the viscera, bringing the walls 10, 12 together to form the anastomosis.

Figure 4:
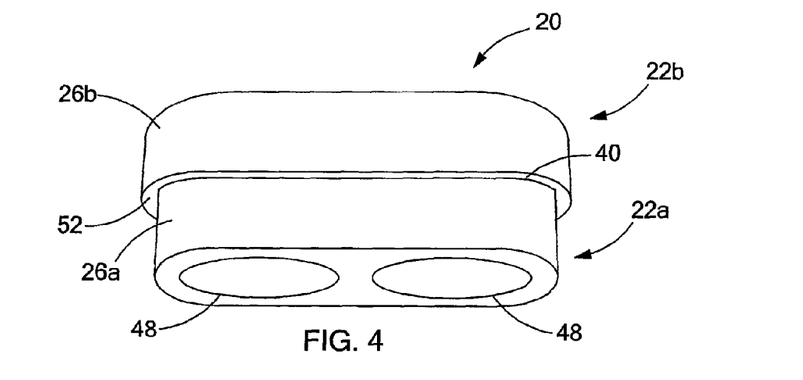
FIG. 4 is a perspective view of the two magnet assemblies of the magnetic anastomosis device of FIG. 1, shown magnetically coupled together.

As best illustrated in FIG. 4, depicting the magnet assemblies 22a, 22b magnetically coupled together outside of a body, one of the magnet assemblies 22a, 22b may be larger than the other. In this embodiment, the magnet assembly 22b is larger than the magnet assembly 22a. For example, the jacket 26b may be between about 1 mm and 5 mm longer in the longitudinal direction than the jacket 26a and between about 1 mm and 5 mm wider in the lateral direction than the jacket 26a. One reason for the difference in the length of the jackets 26a, 26b is the difference in placement of each jacket 26a, 26b. For example, if the magnetic anastomosis device 20 is used to form an anastomosis with the walls of the duodenum 17 and the stomach 16, the larger magnet assembly 22b would be placed in the stomach 16 and the smaller magnet assembly 22a would be placed in the duodenum 17.

In one embodiment, as shown in FIG. 1, the magnets 23a, 24a, 23b, 24b are circular including an outer periphery having a radius of curvature. In this embodiment, the elongate jackets 26a, 26b have two side portions 31 joined by two curved portions 33, each of which has a radius curvature substantially the same as the radius of curvature of the outer peripheries of the magnets 23a, 24a and 23b, 24b disposed within the respective jackets 26a, 26b.

The magnets 23a, 24a, 23b, 24b can be circular, cubular, cylindrical, polygonal, oval or ovoid, square, rectangular or the like as long as they are dimensioned to fit within the jackets 26a, 26b. Preferably, each magnet 23a, 24a, 23b, 24b has a general disc shape (i.e., has an axial height which is less than the outer diameter) with an outer diameter in the range of about 5 mm to about 20 mm, and more preferably in the range of about 12 mm to about 18 mm.

The magnets 23a, 24a and 23b, 24b are preferably a rare-earth magnet, such as Neodymium-iron-boron, cobalt, etc. The jackets 26a, 26b are preferably formed from a nonferrous metal which is press fit or adhesively coupled to the magnets 23a, 24a, and 23b, 24b. In one example, the jackets 26a, 26b are formed from stainless steel. The jackets 26a, 26b may also be formed from any suitable plastic known in the art. The magnet assemblies 22a, 22b may include a protective coating which may be formed of various materials such as polymers like Teflon® or Paralene® for protection of the magnets 23a, 24a and 23b, 24b from the corrosive effects of digestive acids or other bodily fluids depending upon the bodily structure involved.

Figure 5:
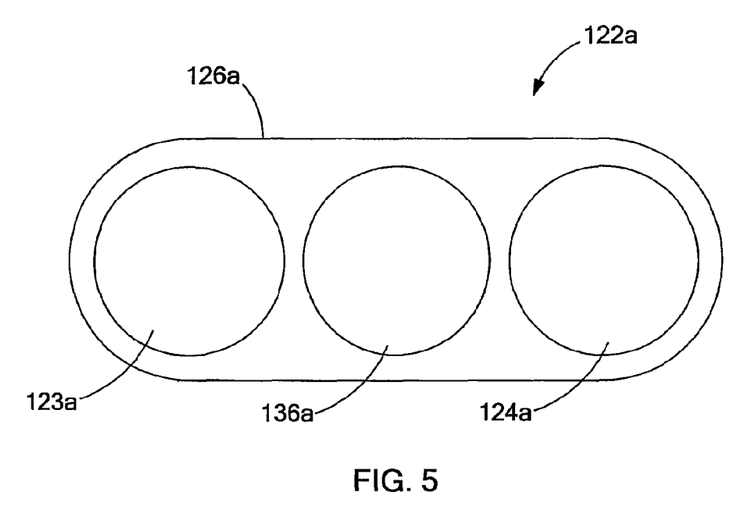
FIG. 5 is a top view of a magnet assembly of a magnetic anastomosis device constructed in accordance with further teachings of the present invention.

While FIGS. 1-4 depict each magnet assembly 22a, 22b having two magnets 23a, 24a and 23b, 24b, a magnet assembly may include three or more magnets without falling beyond the scope of the present invention. For example, as shown in FIG. 5, the magnet assembly 122a has three magnets including a first magnet 123a, a second magnet 124a, and a third magnet 136a disposed therebetween, all of which are encased within the elongate jacket 126a. A magnet assembly 122a in accordance with the teachings of the present invention may comprise more than three magnets, however, as the number of magnets within each magnet assembly 122a increases, the length of the elongate jacket 126a increases, affecting the comfort and ease of delivery of the magnet assembly within the patient. Thus, it may be desirable to use smaller magnets in magnet assemblies having three or more magnets.

By using an elongate magnet assembly 22a, 22b with at least two magnets in each assembly, a larger anastomosis or opening can be formed while assuring proper orientation of one magnet assembly relative to the other. At the same time, the lateral width still allows the assemblies 22a, 22b to be placed perorally, as discussed later herein. Accordingly, the length of each jacket 26a, 26b depends upon the size and number of magnets 23a, 24a and 23b, 24b within each respective magnet assembly 22a, 22b. Each jacket 26a, 26b may have a major axis (longitudinal dimension) in the range of about 12 mm to about 60 mm and a minor axis (lateral dimension) in the range of about 6 mm to about 22 mm. In one preferred embodiment, each jacket 26a, 26b includes two magnets 23a, 24a and 23b, 24b, respectively, and has a major axis in the range of about 26 mm to about 36 mm and a minor axis in the range of about 12 mm to about 18 mm.

Referring to FIG. 6, a magnetic anastomosis device 220 constructed in accordance with the teachings of the present invention is illustrated without magnets disposed within the magnet assemblies 222a, 222b. FIG. 6 illustrates an embodiment of the invention having a description similar to that of FIGS. 1-4 and in which similar components are denoted by similar reference numerals increased by 200. As shown, each magnet assembly 222a, 222b includes a respective elongate jacket 226a, 226b, each of which includes a body portion 245 having opposing planar surfaces 242, 244 and a peripheral surface 246 extending therebetween. The planar surface 244 of the magnet assembly 222b and the planar surface 242 of the magnet assembly 222a are shown in FIG. 6. In this embodiment, each body portion 245 includes two cavities 248 formed therethrough for receiving magnets therein and a third cavity 250 formed therethrough and disposed in between the cavities 248, providing a larger gap 225 separating the magnets. The cavities 248 may be formed by any suitable means in the art and may comprise a circular shape, as shown, or any other suitable shape configured to accommodate the magnets (not shown). The magnets (not shown) are configured to be received within the cavities 248 such that they are flush with the planar surfaces 242, 244 of their respective jacket 226a, 226b.

In this embodiment, the cavity 250 does not receive a magnet therein. Rather, the cavities 250 of the jackets 226a, 226b are left open such that when the magnet assemblies 222a, 222b are in alignment the cavities 250 define a through-hole to create an immediate anastomosis. In one example, once the magnet assemblies 222a, 222b have mated, and the cavities 250 are aligned, a needle is disposed through the cavities 250 of the magnet assemblies 222a, 222b, and thus through the tissue disposed within the cavities 250, and a wire guide is disposed through the needle. The needle may be removed, leaving the wire guide in place. Thereafter, a dilation balloon may be positioned therein and the balloon may be dilated to form an opening in the tissue. Alternatively, a cutting device, e.g., an electro-cautery device or a cutting forceps, may be inserted within the cavities 250 to cut the tissue disposed therein to form the immediate anastomosis. The cavity 250 may be formed by any suitable means in the art and may comprise a rectangular shape, as shown, or any other suitable shape for receiving an appropriate medical device therein to form an opening within the tissue disposed therein.

As further illustrated in FIG. 6, the peripheral surface 246 of the magnet assembly 222b protrudes beyond the planar surface 244 to define a peripheral rim 262. Although not visible in FIG. 6, the peripheral surface 246 of the magnet assembly 222a preferably protrudes beyond the planar surface 242. Additionally, the peripheral surface 246 of each magnet assembly 222a, 222b preferably protrudes in the opposite direction beyond the opposing planar surfaces (the planar surface opposing the planar surface 242 of magnet assembly 222a and the planar surface opposing the planar surface 244 of magnet assembly 222b). Further, each jacket 226a, 226b includes a series of transverse holes 260 formed therethrouh along a longitudinal axis of each jacket 226a, 226b. These holes 260 align with transverse holes formed through the magnets (not shown) that are configured to be received within the jackets 226a, 226b so as to define a lumen which extends through each of the magnet assemblies 222a, 222b for receiving a wire guide or a suture used in positioning of the magnetic anastomosis device 220, an example of which will be discussed in further detail below.

Figure 10:
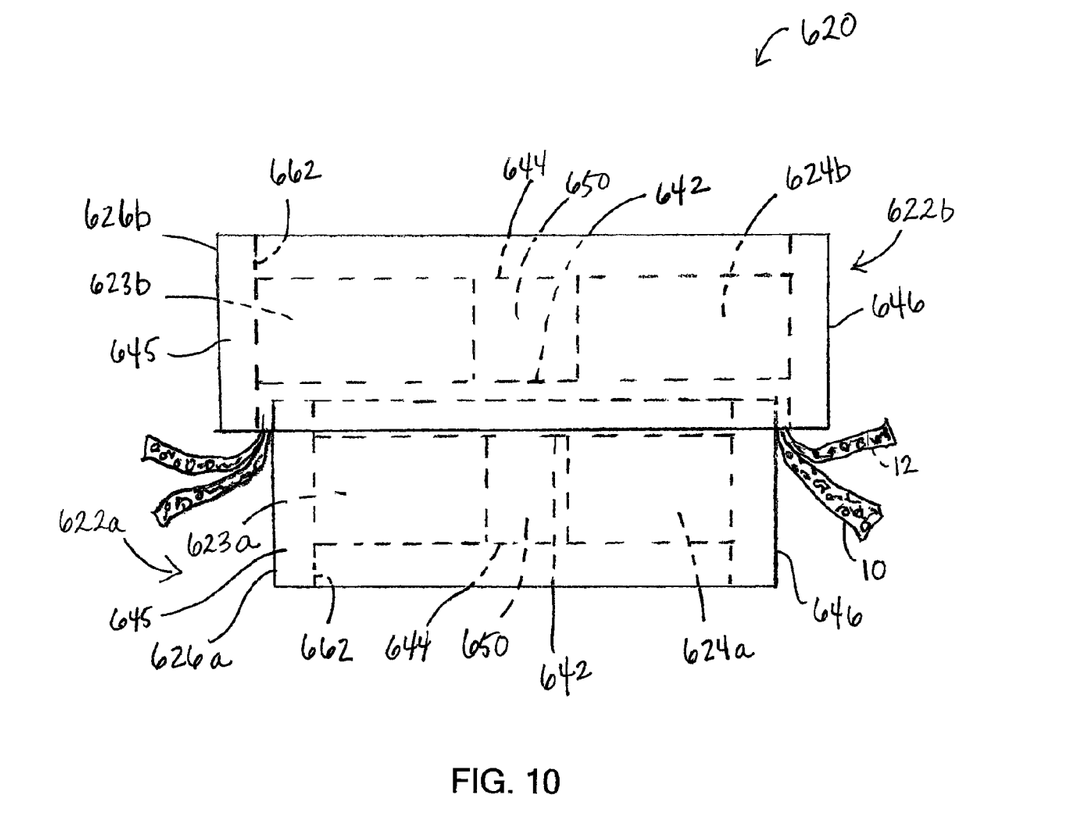
FIG. 10 is a side view of a magnetic anastomosis device constructed in accordance with further teachings of the present invention, shown forming an anastomosis.

FIG. 10 illustrates a magnetic anastomosis 620 device constructed in accordance with further teachings of the present invention having a description similar to that of FIG. 6, in which similar components are denoted by similar reference numerals increased by 400. Each magnet assembly 622a, 622b includes a respective elongate jacket 626a, 626b, each of which includes a body portion 645 having opposing planar surfaces 642 and 644 and a peripheral surface 646 extending therebetween. In this embodiment, each body portion 645 includes two cavities formed therethrough for receiving magnets 623a, 624a, 623b, 624b therein and a third cavity 650 formed therethrough and disposed in between the magnets 623a and 624a of the magnet assembly 622a, and in between the magnets 623b and 624b of the magnet assembly 622b. The magnets 623a, 624a, 623b, 624b are sized to be received within the cavities of each body portion 645 such that they are flush with the planar surfaces 642, 644 of their respective jacket 626a, 626b.

As shown in FIG. 10, the peripheral surface 646 of each jacket 626a, 626b protrudes beyond the planar surfaces 642, 644 to define a peripheral rim 662. In this embodiment, one magnet assembly 622a is smaller than the other magnet assembly 622b. The smaller magnet assembly 622a is sized and configured to fit within the space defined by the peripheral rim 662 of the larger magnet assembly 622b, as depicted in FIG. 10. Thus, when the magnet assemblies 622a, 622b come together by virtue of their magnetic attraction to compress the two bodily walls 10, 12, the peripheral rim 662 of the larger magnet assembly 622b will ensure that the smaller magnet assembly 622a is centered relative to the larger magnet assembly 622a. Accordingly, the smaller magnet assembly 622a is designed to nest within the larger magnet assembly 622b, the peripheral rim 662 of the larger magnet assembly 622b aiding in self-centering alignment, eventually producing the anastomosis by ischemic necrosis. Each of the jackets 626a, 626b preferably includes a series of transverse holes (not shown), like the holes 260 of FIG. 6, to define a lumen which extends through each of the magnet assemblies 622a, 622b for receiving a wire guide or a suture used in positioning of the magnetic anastomosis device 620.

Figure 7:
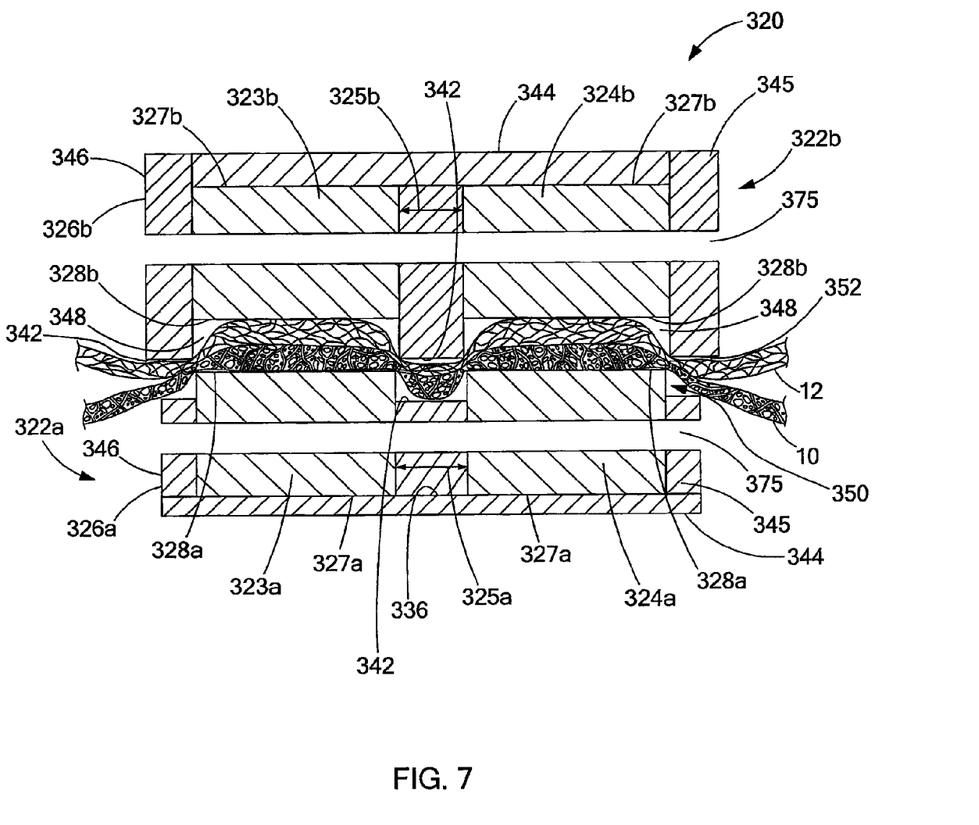
FIG. 7 is a cross-sectional view of a magnetic anastomosis device constructed in accordance with further teachings of the present invention, shown forming an anastomosis.

Referring to FIG. 7, a magnetic anastomosis device constructed in accordance with further teachings of the present invention is illustrated therein and designated at 320. FIG. 7 illustrates an embodiment of the invention having a description similar to that of FIGS. 1-4 and in which similar components are denoted by similar reference numerals increased by 300. In this embodiment, the cavities 348 formed within the body portion 345 of at least one of the jackets 326a, 326b of the respective magnet assemblies 322a, 322b are formed through only one of the planar surfaces 342 or 344. As illustrated in FIG. 7, the cavities 348 of the jackets 326a, 326b are formed through the planar surface 342 and the magnets 323a, 324a, 323b, 324b are disposed on the surface at the bottom of the cavity 348 formed within the body portion 345.

In this embodiment, the magnets 323a, 324a are disposed within the cavities 348 of the jacket 326a such that the faces 328a of the magnets 323a, 324a protrude beyond the planar surface 342 approximately 1 mm, thus defining a peripheral recess 350. As shown in FIG. 7, the cavities are dimensioned such that, with the magnets 323b, 324b disposed therein, the peripheral surface 346 of the magnet assembly 322b protrudes approximately 1 mm above each of the faces 328b (i.e., the planar surface 342 of the jacket 326b is spaced approximately 1 mm from the faces 328b of the magnets 323b, 324b), thus defining a peripheral edge 352.

In FIG. 7, the magnet assemblies 322a and 322b come together to compress the two bodily walls 10 and 12 therebetween to form the anastomosis. As the magnet assemblies 322a and 322b are drawn toward one another, each of the cavities 348 formed within the magnet assembly 322b is sized to receive a portion of the face 328a of one of the magnets 323a, 324a of the magnet assembly 322a. In particular, when the magnet assemblies 322a, 322b are delivered, the faces 328a of the magnets 323a, 324a of the magnet assembly 322a contact the wall 10 of the viscera and the peripheral edge 352 contacts the wall 12 of the adjacent viscera and helps to initiate the ischemic necrosis of the tissue captured between the first and second magnet assemblies 322a, 322b. The space or gap 325a provided between the magnets 323a, 324a of the first magnet assembly 322a helps to trap tissue between the magnet assemblies 322a, 322b to promote tissue necrosis.

It is also within the scope of the present invention for the magnets 323a, 324a and 323b, 324b to be disposed within respective jackets 326a, 326b such that the faces 328a, 328b are flush with the planar surfaces 242 of each of the respective jackets 326a, 326b.

Figure 8A:
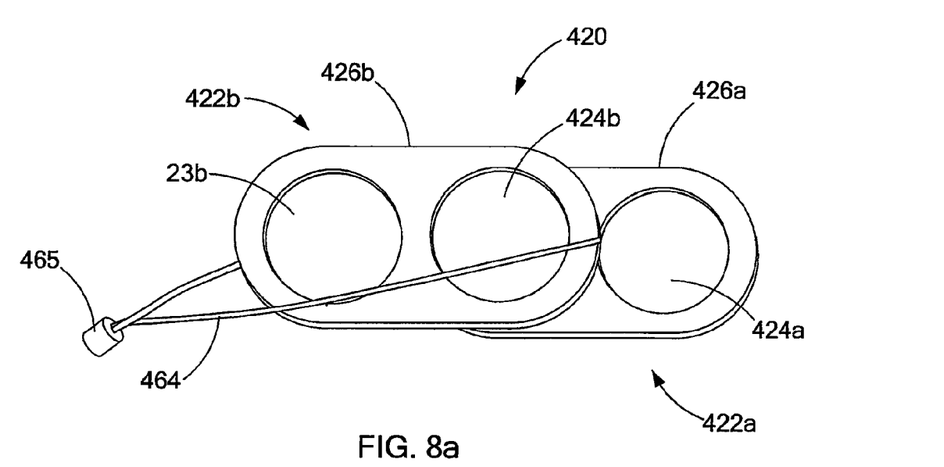
FIG. 8a is a perspective view of a magnetic anastomosis device constructed in accordance with further teachings of the present invention.
Figure 8B:
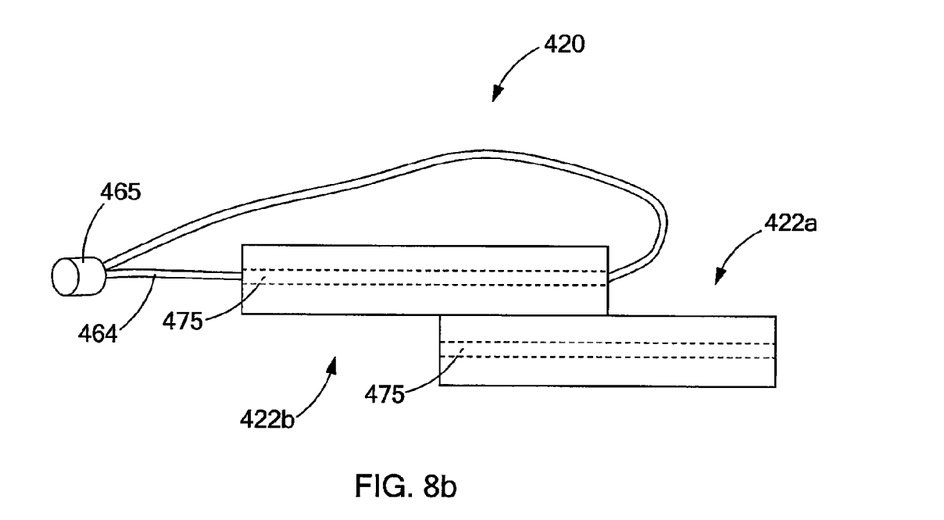

Referring to FIGS. 8a-b, a magnetic anastomosis device constructed in accordance with further teachings of the present invention is illustrated therein and designated at 420. FIGS. 8a-b illustrate an embodiment of the invention having a description similar to that of FIGS. 1-4 and in which similar components are denoted by similar reference numerals increased by 400. In this embodiment, the magnetic anastomosis device includes a suture 464 which aids in the delivery of device as will be described in more detail below. The suture 464 is disposed through a lumen 475 formed through one of the magnet assemblies 422b (i.e., formed through the jacket 426b and the magnets 423b, 424b encased therein). The ends of the suture 464 are joined by an end member 465. As discussed in greater detail below, during positioning of the device 420, the end member 465 may be grasped to manipulate the positioning of the magnetic assembly 422b relative to the magnetic assembly 422a. It is noted that the suture 464 may be attached to the jacket 426b by any other suitable means known in the art. The suture 464 may comprise stainless steel wire or any suitable biocompatible suture material or rope known in art and preferably has a length a little over two times the length of the jacket 426b so that the ends can be joined together by the end member 465 with enough slack to be capable of being grasped by a medical grasping device.

Figure 9A:
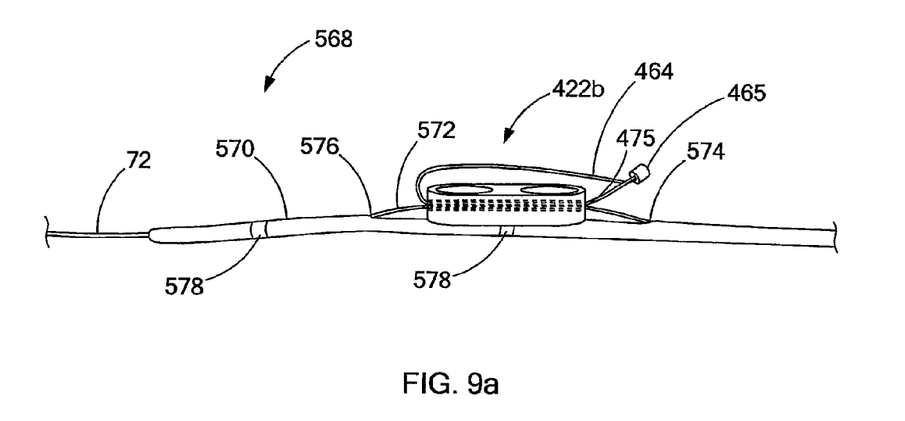
FIG. 9a is a perspective view of a delivery system for delivering a magnetic anastomosis device constructed in accordance with teachings of the present invention.
Figure 9B:
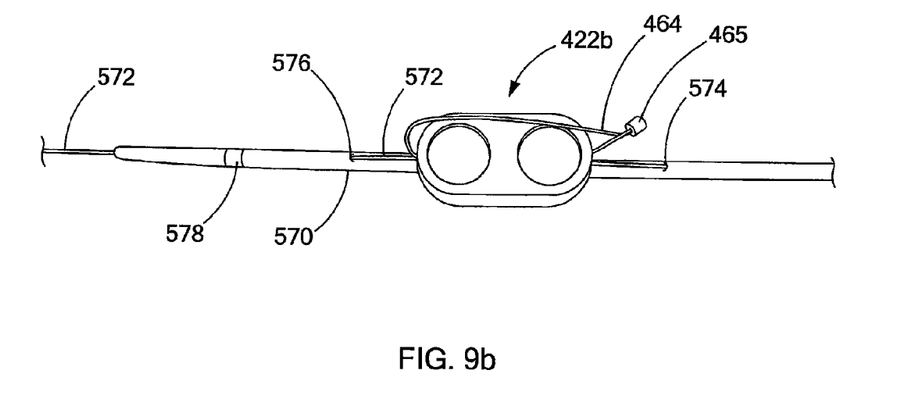

Turning now to FIGS. 9a-b, a delivery system 568 for delivering a magnetic anastomosis device in accordance with the teachings of the present invention is illustrated. The delivery system 568 is shown with the magnet assembly 422b of the magnetic anastomosis device 420 of FIGS. 8a-b, however, the delivery system 568 may be used to deliver any magnetic anastomosis device in accordance with the teachings of the present invention. The delivery system 568 uses a catheter 570 and a wire guide 572 to deliver the magnet assemblies 422a, 422b. As shown in FIGS. 9a and 9b, the catheter 570 has two holes, a proximal hole 574 and a distal hole 576 through which the wire guide 572 is placed. The proximal 574 and distal 576 holes are sufficiently spaced apart to accommodate one of the magnet assemblies 422b between them. The holes 574, 576 are about 25 mm to about 100 mm apart or any subcombination of ranges therein. The preferred distance between the holes 574, 576 will depend on the length, or major axis, and size of the magnet assemblies 422a, 422b. These holes 574, 576 are located in the distal part of the catheter 570 and are appropriately spaced to accommodate magnet assemblies 422a, 422b of various sizes in length. The location of the holes 574, 576 in the wire guide lumen may be modified as required to accommodate the various sizes of the magnet assemblies 422a, 422b, examples of which are provided above. It is noted that the catheter 570 may include more than one lumen, for example, the catheter 570 may include a second lumen for the insertion of a medical grasping instrument or for the insertion of contrast media.

As provided above, for use with this delivery system, the magnet assemblies 422a, 422b include a lumen 475 formed therethrough to accommodate the wire guide 572. Thus, the jackets 426a, 426b and each of the magnets 423a, 424a, and 423b, 424b disposed within respective jackets 426a, 426b have a transverse hole formed therethrough. The holes formed through the magnets 423a, 424a and the jacket 426a are aligned and the holes formed through the magnets 423b, 424b and the jacket 426b are aligned in order to receive the wire guide 572 through the magnet assembly 422a, 422b. In this embodiment, one of the magnet assemblies 422a, 422b includes a suture 464 to aid in the positioning of the magnet assembly 422b with respect to the other magnet assembly 422a. The suture 464 is disposed through the lumen 475, which is the same lumen through which the wire guide 572 is received. Thus, the lumen 475 of the magnet assembly 422b is sized and configured to receive both the suture 464 and the wire guide 572. Alternatively, the magnet assembly 422b may include two separate lumens, one for the wire guide 572 and another for the suture 464.

A radiopaque marker 578 is placed on the catheter 570 in the vicinity of the magnet assembly 422b to mark the magnet assembly 422b location when viewed through fluoroscopy. A radiopaque marker 578 can be placed underneath the magnet assembly 422b on the catheter 570 to mark the location of the magnet assembly 422b when viewing the delivery system from the side.

The wire guide 572 holds the magnet assembly 422b in place on the distal end of the catheter 570. In FIGS. 9a and 9b, the wire guide 572 is shown protruding from the proximal hole 574, going through the lumen 475 of the magnet assembly 22b, and re-entering the catheter 570 at the distal hole 576. The wire guide 572 and the catheter 570 may include radiopaque markers 578 that permit tracking of the delivery system for accurate positioning of the magnet assembly 422b. It may be preferred that a radiopaque marker 578 be placed immediately distal to the magnet assembly 422b. The catheter 570 may be used alone or in conjunction with other wire guide cannulae for navigation of the bodily lumens and delivery of a magnet assembly.

Figure 11:
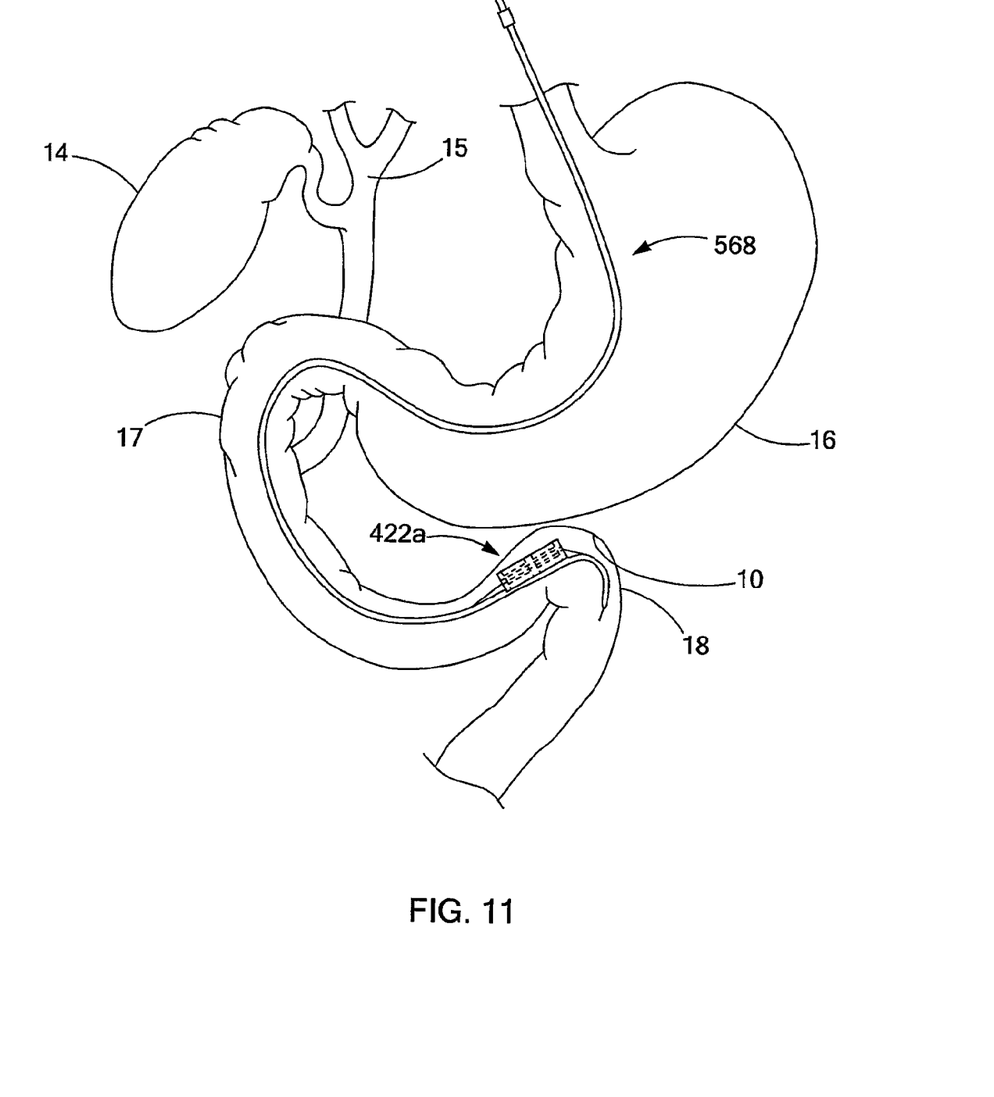
FIGS. 11, 12, and 13 schematically depict the use of two magnet assemblies forming a magnetic anastomosis device in accordance with the teachings of the present invention.

It will be recognized by those skilled in the art that the magnetic anastomosis device 20 employing the magnet assemblies 22a, 22b described herein not only preserves the benefits of improving the time of the procedure to place the magnet assemblies 22a, 22b, but further provides a small delivery configuration which may be easily located within the body for accurate delivery. The delivery systems described herein also provide for insertion of the magnet assemblies 22a, 22b through natural orifices. As such, there is also a method for delivering the magnet assemblies 22a, 22b to a position for forming an anastomosis between two viscera. FIG. 11 shows the relative positions of several viscera in the abdominal cavity, including the gall bladder 14, the common bile duct 15, the stomach 16, the duodenum 17, and the jejunum 18 of the small intestine. Although not shown, the delivery system 568 described herein can also be used to implant anastomosis-forming magnet assemblies in the colon for possible use in gastric bypass procedures. The delivery system 568 described herein can be used, for example, to create an anastomosis between the stomach 16 and the jejunum 18 of the small intestine. The delivery system 568 can also be used as a part of procedure where forceps are used to place one of the magnet assemblies.

A method for delivering a magnet assembly to form an anastomosis comprises introducing the delivery system 568 into an endoluminal vessel. FIG. 11 shows the system 568 being advanced to the jejunum 18. The delivery of the magnet assembly 422a follows once the wire guide 572 has been positioned adjacent the first wall 10 of a first viscus. In FIG. 11, the first viscus is the jejunum 18. The magnet assembly 422a is placed on the catheter 570 as shown in FIGS. 9a and 9b and held in place on the catheter 570 by the wire guide 572. The wire guide 572 is loaded through the catheter 570, passing through distal hole 576 in the catheter 570 lumen, through the lumen 475 of the magnet assembly 422a, and then reentering the catheter 570 lumen through proximal hole 574. Using the radiopaque markers 578 as a guide, the catheter 570 is advanced such that the magnet assembly 422a is placed adjacent to the wall 10 of the jejunum 18 as shown in FIG. 12.

Figure 12:
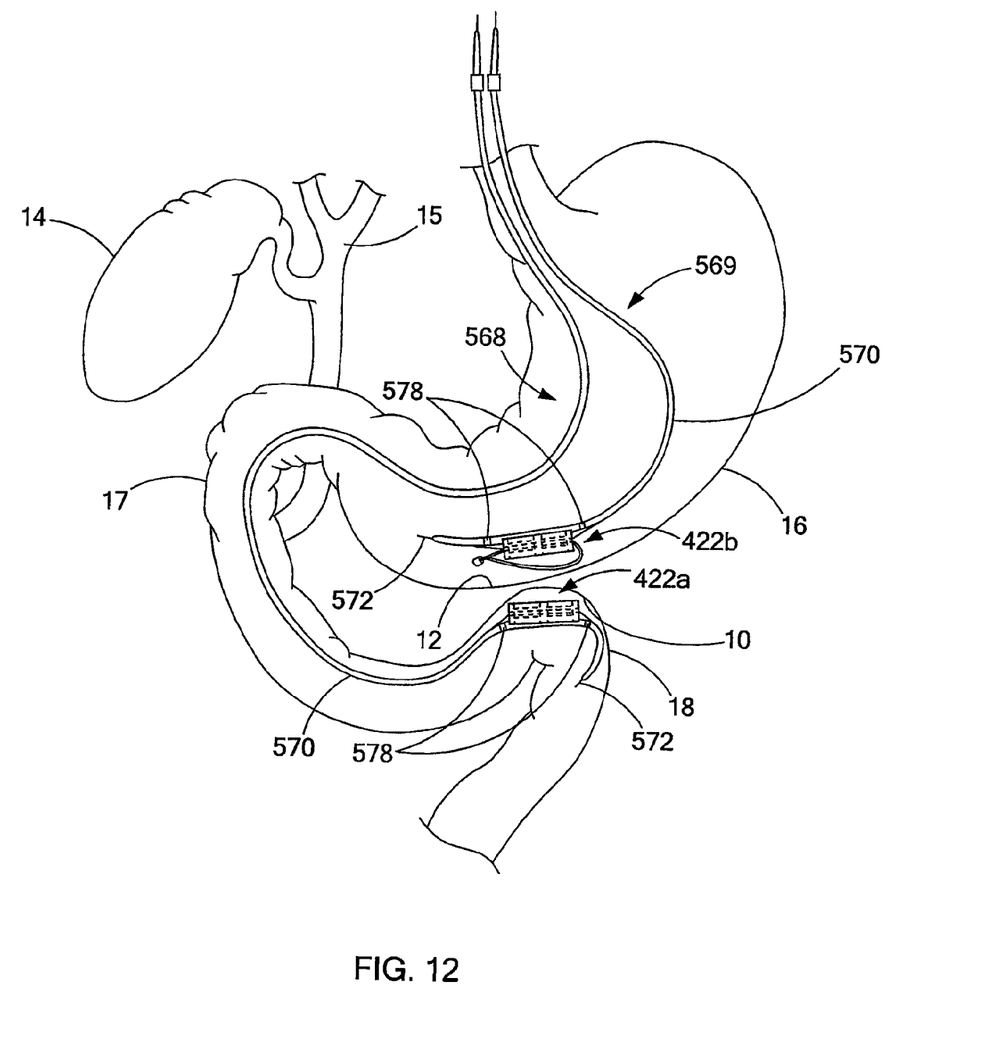
Figure 13:
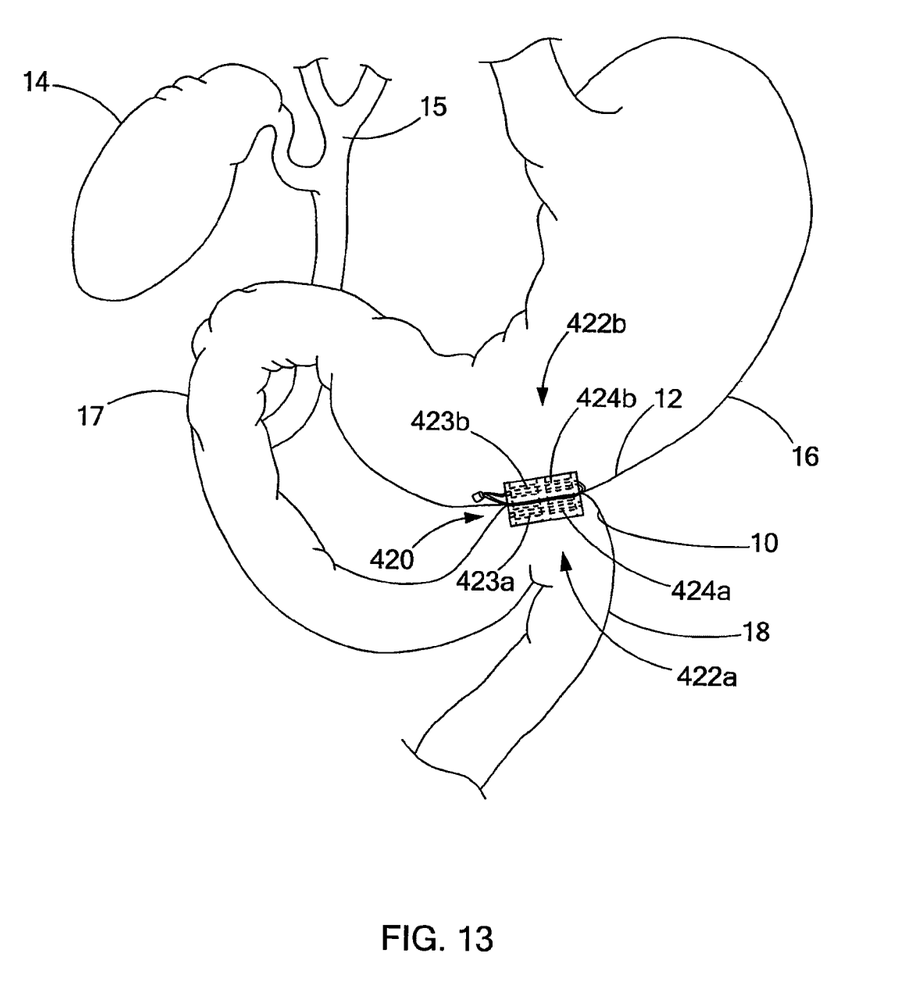

The delivery system 568 with magnet assembly 422a remains in position as a second delivery system 569 is introduced into the stomach 16 as shown in FIG. 12. The magnet assembly 422b is positioned adjacent the wall 12 of the stomach 16 that borders the jejunum 18 near the location of the magnet assembly 422a. The magnetic forces of the magnets 423a, 424a and 423b, 424b disposed therein attract the magnet assemblies 422a, 422b together, compressing the walls 10, 12 together of the jejunum 18 and the stomach 16. To release the magnet assemblies 422a, 422b, the operator removes the wire guide 572 and then the catheter 570. As described in more detail above, FIG. 3 illustrates an enlarged view of a magnetic anastomosis device 20 compressing the walls 10, 12 together.

The magnetic forces of the magnets 423a, 424a and 423b, 424b draw the magnet assemblies 422a, 422b toward one another, preferably so that each of the magnets 432a and 424a opposes one of the magnets 423b and 424b. In the instance where the magnet assemblies 422a, 422b do not align in this fashion, for example, in FIGS. 8a and 8b, where only one of the magnets 424b of the magnet assembly 422b opposes only one of the magnets 423a (not shown) of the magnet assembly 422a, the suture 464 may be used to place the magnet assemblies 422a, 422b in proper alignment. In this fashion, a grasping forceps or any other suitable medical grasping device (not shown) may be used to manipulate the magnet assembly 422b relative to the magnet assembly 422a by grasping the end member 465 of the suture 464 and either pulling, pushing, or rotating the magnet assembly 422b relative to the magnet assembly 422a to place the magnet assemblies 422a, 422b in proper alignment.

The radiopaque markers 578 can be used as a guide to help position the magnet assemblies 422a, 422b in the correct orientation under fluoroscopy. As will be recognized by those skilled in the art, placement of the magnet assemblies 422a, 422b may be aided by fluoroscopy, ultrasound, fiber optic imaging or other well known guidance techniques.

Once the necrosis of the walls 10, 12 of the jejunum and the stomach is complete, an anastomosis is formed. The magnet assemblies 422a, 422b can then pass through the body naturally or can be removed by means such as laparotic removal, endoscopic removal, or other procedure.

It will be recognized by those skilled in the art that the larger, elongate magnet assemblies 22a, 22b of the present invention are capable of being delivered with the same small delivery configuration as prior art magnet assemblies, but also provide the advantage of reducing the probability of the anastomosis being closed over time and eliminating the need to intervene the patient for a second procedure to place a stent in the anastomosis to prevent closure thereof. Moreover, those skilled in the art will recognize the centering and alignment advantages of having two magnets 23a, 24a and 23b, 24b disposed within each of the respective magnet assemblies 22a, 22b.

It will be recognized by those skilled in the art that, while the devices and methods described above generally include placing the devices in tissue through an internal bodily lumen, it will be recognized that the systems, devices and methods may be used on any layer of material (e.g. fabrics, cloth, polymers, elastomers, plastics and rubber) that may or may not be associated with a human or animal body and a bodily lumen. For example, the systems, devices and methods can find use in laboratory and industrial settings for placing devices through one or more layers of material that may or may not find application to the human or animal body, and likewise forming/connecting holes or perforations in layers of material that are not bodily tissue. Some examples include sewing or stitching and related manufacturing, working with synthetic tissues, connecting or repairing polymeric sheets, animal studies, veterinary applications, and post-mortem activities.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A magnetic anastomosis device used for forming an anastomosis between two bodily walls, the device comprising:
    a first magnet assembly including a first magnet and a second magnet disposed within a first jacket, the first jacket including a first body portion having a first and a second cavity formed therethrough, the first and second magnets disposed within the respective first and second cavities; and
    a second magnet assembly including a third magnet and a fourth magnet disposed within a second jacket, the second jacket including a second body portion having a third and a fourth cavity formed therethrough, the third and fourth magnets disposed within the respective third and fourth cavities, wherein the first and second magnet assemblies are configured to be magnetically coupled to compress the two bodily walls therebetween to form the anastomosis.

2. The device of claim 1, wherein each of the first and second jackets has an elongate shape defining respective first and second longitudinal axes and first and second lateral axes.

3. The device of claim 2, wherein the first and second magnets are oriented on the first longitudinal axis of the first jacket and wherein the third and fourth magnets are oriented on the second longitudinal axis of the second jacket.

4. The device of claim 3, wherein the first and second magnets are spaced apart from one another on different sides of the first lateral axis, and wherein the third and fourth magnets are spaced apart from one another on different sides of the second lateral axis.

5. The device of claim 2, wherein each of the first and second jackets has a longitudinal dimension in the range of about 12 mm to about 60 mm and a lateral dimension in the range of about 6 mm to about 22 mm.

6. The device of claim 1, wherein each of the first, second, third, and fourth magnets has a disc shape having an outer diameter in the range of about 5 mm to about 20 mm.

7. The device of claim 1, wherein the first jacket includes a fifth cavity formed through the first body portion between the first and the second cavities and the second jacket includes a sixth cavity formed through the second body portion between the third and fourth cavities, wherein the fifth and sixth cavities define an open cavity of the device for access to the bodily walls disposed between the first and second magnet assemblies.

8. The device of claim 1, wherein at least one of the first and second body portions includes a first planar surface and an opposing second planar surface and a peripheral surface extending therebetween, the cavities being formed through the first and second planar surfaces, wherein the peripheral surface extends beyond at least one of the first and second planar surfaces to define a peripheral rim.

9. The device of claim 1, wherein each of the first, second, third, and fourth magnets includes a respective first, second, third, and fourth face, each of the first and second faces having a magnetic attraction to at least one of the third and fourth faces, wherein the first and second jackets are configured to compress the two bodily walls therebetween during magnetic attraction to form the anastomosis.

10. The device of claim 9, wherein the first and third faces are north pole and the second and fourth faces are south pole.

11. A magnetic anastomosis device used for forming an anastomosis between two bodily walls, the device comprising:
    a first magnet assembly including a first magnet and a second magnet disposed within a first jacket;
    a second magnet assembly including a third magnet and a fourth magnet disposed within a second jacket, wherein the first and second magnet assemblies are configured to be magnetically coupled to compress the two bodily walls therebetween to form the anastomosis; and
    wherein the first jacket and each of the first and second magnets includes a transverse hole formed therethrough to define a first lumen of the first magnet assembly, wherein the second jacket and each of the third and fourth magnets includes a transverse hole formed therethrough to define a second lumen of the second magnet assembly.

12. The device of claim 11, wherein the first and second lumens are configured for receiving a wire guide.

13. The device of claim 12, wherein the first and second ends are joined together at an end member, wherein the end member is configured for manipulation by a medical device to manipulate at least one magnet assembly relative to the other magnet assembly.

14. The device of claim 11, further comprising a suture having a first end and a second end, the suture being disposed within at least one of the first and second lumens, wherein the first and second ends of the suture are joined together outside of the at least one of the first and second lumens.

15. A magnetic anastomosis device used for forming an anastomosis between two bodily walls, the device comprising:
    a first magnet;
    a second magnet;
    a third magnet;
    a fourth magnet;
    a first jacket encasing the first and second magnets, the first jacket having an elongate shape defining a first longitudinal axis, the first and second magnets oriented on the first longitudinal axis;
    a second jacket encasing the third and fourth magnets, the second jacket having an elongate shape defining a second longitudinal axis, the third and fourth magnets oriented on the second longitudinal axis; and
    a suture attached to at least one of the first and second jackets for manipulation of one of the first and second jackets relative to the other; wherein the first and second jackets are configured to be magnetically coupled to compress the two bodily walls therebetween to form the anastomosis.

16. The device of claim 15, wherein each of the first and second jackets has a shape in the form of one of an ellipse shape, an oval shape, an egg shape, a kidney shape, a figure eight shape, and a rectangle with rounded corners.

17. The device of claim 15, wherein each of the first, second, third, and fourth magnets has a circular shape having a diameter in the range of about 5 mm to about 20 mm, and wherein each of the first and second jackets has a width in the range of about 6 mm to about 22 mm and a length in the range of about 12 mm to about 60 mm.

18. The device of claim 15, wherein the first jacket includes a first body portion including a first planar surface, an opposing second planar surface, a peripheral surface extending therebetween, and at least two cavities formed through the first and second planar surfaces, each of the first and second magnets being disposed within one of the cavities, wherein the peripheral surface protrudes beyond at least one of the first and second planar surfaces to define a peripheral rim.

\* \* \* \* \*